US012351538B2

(12) United States Patent
Richter et al.

(10) Patent No.: US 12,351,538 B2
(45) Date of Patent: Jul. 8, 2025

(54) PROCESS FOR ACID HYDROLYSIS OF PURE POLYLAUROLACTAM

(71) Applicant: Evonik Operations GmbH, Essen (DE)

(72) Inventors: Alexander Richter, Haltern am See (DE); Christian Nörnberg, Hamburg (DE); Norbert Kern, Haltern (DE); Florian Hermes, Haltern am See (DE); Franz-Erich Baumann, Duelmen (DE); Martin Roos, Haltern am See (DE); Daniel Demicoli, Essen (DE)

(73) Assignee: Evonik Operations GmbH, Essen (DE)

( * ) Notice: Subject to any disclaimer, the term of this patent is extended or adjusted under 35 U.S.C. 154(b) by 364 days.

(21) Appl. No.: 18/245,317

(22) PCT Filed: Sep. 14, 2021

(86) PCT No.: PCT/EP2021/075148
§ 371 (c)(1),
(2) Date: Mar. 14, 2023

(87) PCT Pub. No.: WO2022/058291
PCT Pub. Date: Mar. 24, 2022

(65) Prior Publication Data
US 2024/0018092 A1 Jan. 18, 2024

(30) Foreign Application Priority Data
Sep. 16, 2020 (EP) .................................. 20196421

(51) Int. Cl.
*C07C 227/20* (2006.01)
*C07C 227/22* (2006.01)

(52) U.S. Cl.
CPC .......... *C07C 227/20* (2013.01); *C07C 227/22* (2013.01)

(58) Field of Classification Search
None
See application file for complete search history.

(56) References Cited

U.S. PATENT DOCUMENTS

| | | | |
|---|---|---|---|
| 2,407,896 A | 9/1946 | Myers | |
| 2,840,606 A | 6/1958 | Miller | |
| 2,872,420 A | 2/1959 | Kruyff | |
| 3,069,465 A | 12/1962 | Monet | |
| 3,113,966 A * | 12/1963 | Formaini | C07C 227/22 562/553 |
| 4,170,588 A | 10/1979 | Hegenberg et al. | |
| 5,519,097 A | 5/1996 | Meyer et al. | |
| 5,750,791 A | 5/1998 | Davis et al. | |
| 5,905,168 A | 5/1999 | Dos Santos et al. | |
| 5,932,687 A | 8/1999 | Baumann et al. | |
| 6,794,048 B2 | 9/2004 | Schmitz et al. | |
| 7,211,615 B2 | 5/2007 | Baumann et al. | |
| 8,066,933 B2 | 11/2011 | Monsheimer et al. | |
| 8,232,333 B2 | 7/2012 | Haeger et al. | |
| 8,303,873 B2 | 11/2012 | Dowe et al. | |
| 8,399,658 B2 | 3/2013 | Hengstermann et al. | |
| 8,449,809 B2 | 5/2013 | Monsheimer et al. | |
| 8,574,697 B2 | 11/2013 | Dowe et al. | |
| 8,614,005 B2 | 12/2013 | Wursche et al. | |
| 8,865,053 B2 | 10/2014 | Monsheimer et al. | |
| 8,999,086 B2 | 4/2015 | Bollmann et al. | |
| 9,919,494 B2 | 3/2018 | Franosch et al. | |
| 10,005,885 B2 | 6/2018 | Monsheimer et al. | |
| 10,040,938 B2 | 8/2018 | Nitsche et al. | |
| 10,406,745 B2 | 9/2019 | Baumann et al. | |
| 10,836,903 B2 | 11/2020 | Peirick et al. | |
| 11,117,837 B2 | 9/2021 | Diekmann et al. | |
| 2002/0082352 A1 | 6/2002 | Schmitz et al. | |
| 2005/0038201 A1 | 2/2005 | Wursche et al. | |
| 2007/0036998 A1 | 2/2007 | Dowe et al. | |
| 2007/0104971 A1 | 5/2007 | Wursche et al. | |
| 2008/0116616 A1 | 5/2008 | Monsheimer et al. | |
| 2008/0166496 A1 | 7/2008 | Monsheimer et al. | |
| 2008/0249237 A1 | 10/2008 | Hager et al. | |
| 2008/0261010 A1 | 10/2008 | Wursche et al. | |
| 2010/0300573 A1 | 12/2010 | Dowe et al. | |
| 2011/0124855 A1 | 5/2011 | Hengstermann et al. | |
| 2011/0217559 A1 | 9/2011 | Bollmann et al. | |
| 2011/0250156 A1 | 10/2011 | Jha et al. | |
| 2012/0041132 A1 | 2/2012 | Monsheimer et al. | |
| 2012/0094116 A1 | 4/2012 | Wursche et al. | |
| 2012/0264877 A1 | 10/2012 | Häger et al. | |
| 2012/0315483 A1 | 12/2012 | Baumann et al. | |

(Continued)

FOREIGN PATENT DOCUMENTS

| | | |
|---|---|---|
| CN | 102399363 | 4/2012 |
| DE | 1240 087 | 5/1967 |

(Continued)

OTHER PUBLICATIONS

European Search Report dated Mar. 12, 2021, in European Application No. 20196421.0, 6 pages.
International Search Report dated Jan. 4, 2022, in PCT/EP2021/075148, with English translation, 7 pages.
Written Opinion dated Jan. 4, 2022, in PCT/EP2021/075148, with English translation, 10 pages.
U.S. Pat. No. 6,794,048, Sep. 21, 2004, 2002/0082352, Schmitz et al.
U.S. Appl. No. 10/918,343, filed Aug. 16, 2004, 2005/0038201, Wursche et al.
U.S. Pat. No. 8,066,933, Nov. 29, 2011, 2008/0116616, Monsheimer et al.

(Continued)

*Primary Examiner* — Amy C Bonaparte
(74) *Attorney, Agent, or Firm* — Grüneberg and Myers PLLC

(57) ABSTRACT

An improved process can be used for the acid hydrolysis of polylaurolactam with sulfuric acid. An especially suitable starting material is polylaurolactam which is intended for recycling and which is characterized by a low laurolactam content.

10 Claims, No Drawings

(56) References Cited

U.S. PATENT DOCUMENTS

| | | |
|---|---|---|
| 2014/0037937 A1 | 2/2014 | Wursche et al. |
| 2014/0371364 A1 | 12/2014 | Monsheimer et al. |
| 2015/0086737 A1 | 3/2015 | Nitsche et al. |
| 2015/0086738 A1 | 3/2015 | Nitsche et al. |
| 2016/0060459 A1 | 3/2016 | Franosch et al. |
| 2018/0036938 A1 | 2/2018 | Baumann et al. |
| 2018/0044520 A1 | 2/2018 | Peirick et al. |
| 2018/0093925 A1 | 4/2018 | Diekmann et al. |
| 2018/0094103 A1 | 4/2018 | Diekmann et al. |
| 2019/0016668 A1 | 1/2019 | Hu |
| 2019/0275731 A1 | 9/2019 | Baumann et al. |
| 2021/0371346 A1 | 12/2021 | Diekmann et al. |
| 2022/0227932 A1 | 7/2022 | Weinelt et al. |

FOREIGN PATENT DOCUMENTS

| | | |
|---|---|---|
| DE | 3407 415 | 9/1985 |
| DE | 44 21 454 | 12/1995 |
| DE | 10 2021 203 743 | 10/2022 |
| JP | S53-28642 | 3/1978 |
| JP | 55-108453 | 8/1980 |
| JP | 2008081524 | 4/2008 |
| WO | 2023/041710 | 3/2023 |

OTHER PUBLICATIONS

U.S. Pat. No. 8,449,809, May 28, 2013, 2012/0041132, Monsheimer et al.

U.S. Pat. No. 8,865,053, Oct. 21, 2014, 2008/0166496, Monsheimer et al.

U.S. Pat. No. 10,005,885, Jun. 26, 2018, 2014/0371364, Monsheimer et al.

U.S. Pat. No. 8,232,333, Jul. 31, 2012, 2008/0249237, Haeger et al.

U.S. Appl. No. 13/494,082, filed Jun. 12, 2012, 2012/0264877, Häger et al.

U.S. Appl. No. 11/816,556, filed Jan. 28, 2008, 2008/0261010, Wursche et al.

U.S. Pat. No. 8,614,005, Dec. 24, 2013, 2012/0094116, Wursche et al.

U.S. Appl. No. 14/050,901, filed Oct. 10, 2013, 2014/0037937, Wursche et al.

U.S. Pat. No. 8,303,873, Nov. 6, 2012, 2007/0036998, Dowe et al.

U.S. Appl. No. 11/586,526, filed Oct. 26, 2006, 2007/0104971, Wursche et al.

U.S. Pat. No. 8,999,086, Apr. 7, 2015, 2011/0217559, Bollmann et al.

U.S. Pat. No. 8,574,697, Nov. 5, 2013, 2010/0300573, Dowe et al.

U.S. Pat. No. 8,399,658, Mar. 19, 2013, 2011/0124855, Hengstermann et al.

U.S. Appl. No. 13/081,779, filed Apr. 7, 2011, 2011/0250156, Jha et al.

U.S. Appl. No. 13/581,085, filed Aug. 24, 2012, 2012/0315483, Baumann et al.

U.S. Pat. No. 10,406,745, Sep. 10, 2019, 2018/0036938, Baumann et al.

U.S. Appl. No. 16/422,345, filed May 24, 2019, 2019/0275731, Baumann et al.

U.S. Pat. No. 10,040,938, Aug. 7, 2018, 2015/0086737, Nitsche et al.

U.S. Appl. No. 14/489,632, filed Sep. 18, 2014, 2015/0086738, Nitsche et al.

U.S. Pat. No. 9,919,494, Mar. 20, 2018, 2016/0060459, Franosch et al.

U.S. Pat. No. 10,836,903, Nov. 17, 2020, 2018/0044520, Peirick et al.

U.S. Pat. No. 11,117,837, Sep. 14, 2021, 2018/0093925, Diekmann et al.

U.S. Appl. No. 17/399,281, filed Aug. 11, 2021, 2021/0371346, Diekmann et al.

U.S. Appl. No. 15/718,069, filed Sep. 28, 2017, 2018/0094103, Diekmann et al.

U.S. Appl. No. 17/611,251, filed Nov. 15, 2021, 2022/0227932, Weinelt et al.

* cited by examiner

PROCESS FOR ACID HYDROLYSIS OF PURE POLYLAUROLACTAM

CROSS-REFERENCE TO RELATED APPLICATIONS

This application is the National Stage entry under § 371 of International Application No. PCT/EP2021/075148, filed on Sep. 14, 2021, and which claims the benefit of priority to European Application No. 20196421.0, filed on Sep. 16, 2020. The content of each of these applications is hereby incorporated by reference in its entirety.

BACKGROUND OF THE INVENTION

Field of the Invention

The present invention relates to an improved process for the acidic hydrolysis of polylaurolactam with sulfuric acid. A suitable starting material in particular is polylaurolactam which is intended to be recycled and features a low content of laurolactam.

Description of Related Art

Polylaurolactam (CAS No.: 24937-16-4; alternative names: nylon 12, polyamide 12, hereinafter abbreviated to "PA12") is an industrially important polymer.

PA12 comprises repeating units with the following structure (I), wherein the bond identified with (*) of one repeating unit binds to that identified with (**) of the adjacent repeating unit.

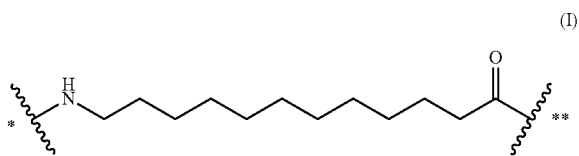

(I)

PA12 is valued in applications, inter alia, for its hydrolysis stability and clearly differs in this property from short-chain polyamides such as polycaprolactam (CAS No. 25038-54-4; alternative name: polyamide 6; hereinafter abbreviated to "PA6") or poly(N,N'-hexamethyleneadipinediamide)/poly(hexamethyleneadipamide) (CAS No.: 32131-17-2; alternative name polyamide 66; hereinafter abbreviated to "PA66").

Due to the higher density of amide groups, PA6 and PA66 absorb several times as much water. In addition, the reaction equilibrium for short-chain polyamides is far further to the side of the monomers, meaning that hydrolysis can proceed much faster.

Recycling of these materials requires cleavage of the amide bond, which is typically performed under acid or base catalysis, in order to obtain defined monomer units.

The first approaches to chemically recycling nylon 66 were pursued as soon as these materials existed.

U.S. Pat. No. 2,872,420 describes a process for recovering nylon 66 from wastes using sulfuric acid. Sulfuric acid of high purity according to this document has only a minor influence on the molecular weight of polyamides and can thus be used for purification by dissolution and precipitation.

The recycling of nylon 6 is a special case since the monomer caprolactam can be separated off from the reaction mixture by distillation and the reaction can thus be brought to a high conversion even with a non-quantitative addition of acid or base.

The treatment of PA6 and PA66 with bases or mineral acids at relatively high temperatures in the presence of water leads to the degradation of the PA6 and PA66 into the monomer units.

U.S. Pat. Nos. 2,407,896 A and 3,069,465 A describe the hydrolysis of PA 66 with sulfuric acid.

WO 97/00846 A1 describes the hydrolysis of PA66 with nitric acid.

U.S. Pat. No. 2,840,606 A describes the alkaline hydrolysis of short-chain AABB-type polyamides. Under alkaline catalysis, the diamine and the diacid are reformed as components at temperatures of greater than 160° C. Addition of aliphatic alcohols accelerates the reaction.

During the hydrolysis of PA6 with the processes described in the prior art, workup of aqueous solutions of this amino acid is difficult since the short-chain ω-aminocarboxylic acids are readily soluble both as salt and as free acid, and therefore purification requires the distillation of large amounts of water.

CN102399363 A describes the hydrolysis of nylon-6 by hydrolytic degradation over solid acids having $SO_4^{2-}$ groups. A route for producing hotmelt adhesives therefrom is described. The reaction is not brought to complete conversion.

DE1240087B describes the workup of longer-chain ω-aminocarboxylic acids such as ω-aminododecanoic acid.

The hydrolytic recycling of polyamide 12 is more technically demanding due to its relatively high stability.

JPS55-108453 A describes the degradation of polyamide 12 by addition of water and phosphoric acid during extrusion. However, this involves lust the reduction of molecular weight down to a value lying above the value of the monomer. Accordingly, this degradation does not proceed to aminolauric acid.

DE 693 09 709 T2 describes the hydrolysis and oxidation of polyamides. Mention is made, as possible polyamides, of PA6, PA66 and PA12. The reaction is based on the fact that nitroso groups are dissolved in the hydrolysis medium.

DE 3401415 A describes the workup of a waste stream from laurolactam production. This waste stream consists of a mixture of lauroiactam, oligoamides and polyamides, and other impurities. Acid- or base-catalysed hydrolysis allows conversion to ω-aminolauric acid.

It has now been found that the hydrolysis in the process described in DE 3401415 A was made easier by means of laurolactam as plasticizer. However, in most cases, PA-12 waste materials do not include laurolactam.

In addition, U.S. Pat. No. 4,170,588 A describes a process for the hydrolysis of polylaurolactam with sulfuric acid at 80° C.

SUMMARY OF THE INVENTION

The object of the present invention accordingly consisted in providing an improved process for hydrolysis of polyimide 12 waste materials.

A process which achieves this object has now surprisingly been found.

The present invention accordingly relates to a process for the hydrolysis of polylaurolactam,
wherein polylaurolactam is cleaved with sulfuric acid at a temperature of from 125° C. to 190° C., preferably 140° C.

to 180° C., more preferably 150° C. to 170° C., even more preferably 160° C. to 165° C., to give ω-aminolauric acid.

DETAILED DESCRIPTION OF THE INVENTION

It has surprisingly been found that the hydrolysis of polylaurolactam with sulfuric acid proceeds with a higher yield compared to the processes described in the prior art.

The polylaurolactam which is used in the process according to the invention is not subject to further restriction. Preference is given to using material intended for recycling (PA12 waste).

The polylaurolactam is used in particular as a powder, since thereby the enlargement of the surface area can accelerate the hydrolysis. A suitable pulverulent PA12 is described for example in EP 0 911 142 A1, To this end, PA12 can be ground to powder by methods known to those skilled in the art before it is used in the process according to the invention.

The PA12 used according to the invention comprises repeating units with the aforementioned structure (I), wherein the bond identified with (*) of one repeating unit binds to that identified with (**) of the adjacent repeating unit.

The PA12 used according to the invention preferably has a molar mass of 1000 to $10^6$ g/mol, more preferably of 3000 to 200 000 g/mol, yet more preferably of 15 000 to 150 000 g/mol, more preferably still 25 000 to 120 000 g/mol, even more preferably 40 000 to 95 000 g/mol, even more preferably still 80 000 g/mol.

The present invention is particularly suitable for the hydrolysis of polylaurolactam comprising a low content of laurolactam. Preferably, polylaurolactam is used which has a content of laurolactam of <4.9% by weight, preferably <4.0% by weight, more preferably <3.0% by weight, yet more preferably <1.0% by weight, even more preferably <0.01% by weight, based in each case on the sum of the masses of PA12 and laurolactam.

The present invention is particularly suitable for the hydrolysis of polylaurolactam comprising a low content of ω-aminclauric acid. Preferably, polylaurolactam is used which has a content of ω-aminolauric acid of <4.9% by weight, preferably <4.0% by weight, more preferably <3.0% by weight, yet more preferably <1.0% by weight, even more preferably <0.3% by weight, based in each case on the sum of the masses of PA12 and ω-aminolauric acid.

This distinguishes the present process in particular from the process in DE 3401415 A, in which residues from the production of laurolactam are hydrolysed, which leads to a high proportion of laurolactam in the reactant to be hydrolysed.

In contrast, hydrolysis with sulfuric acid in the process according to the invention is particularly well suited to the use of material to be recycled which features a low content of laurolactam and ω-aminolauric acid.

The hydrolysis can be performed by processes known to those skilled in the art.

The temperature in the process according to the invention is 125° C. to 190° C., preferably 140° C. to 180° C., more preferably 150° C. to 170° C., even more preferably 160° C. to 165° C.

The pressure in the process according to The invention is preferably in the range 1 bar to 100 bar, preferably 10 bar to 60 bar.

Typically, the polylaurolactam to be hydrolysed is initially charged in a reaction vessel, for example an autoclave coated with a noble metal such as gold or stainless steel, and the sulfuric acid is added thereto.

The sulfuric acid is in this case usually an aqueous solution, the content of sulfuric acid in the aqueous solution not being subject to further restriction.

The content of sulfuric acid in the aqueous solution is preferably in the range 10% to 90% by weight, preferably 20% to 80% by weight, more preferably 30% to 50% by weight, even more preferably 35% to 40% by weight.

The ratio of sulfuric acid used to polylaurolactam used is likewise not subject to further restriction. In particular, sulfuric acid is used in such an amount that the ratio of the weights of sulfuric acid used to PA12 used is in the range 1:0.1 to 1:1, preferably in the ramie 1:0.2 to 1:0.8, more preferably in the range 1:0.3 to 1:0.7, even more preferably in the range 1:0.4 to 1:0.6, even more preferably still in the range 1:0.45 to 1:0.51.

The process according to the invention is preferably performed until at least 30% by weight, more preferably at least 50% by weight, even more preferably at least 70% by weight, more preferably still at least 90% by weight, even more preferably still at least 99% by weight of the PA12 used has reacted.

In an alternative particular embodiment of the process according to the invention, after 1-99% by weight, preferably 30-90% by weight, more preferably 50-70% by weight, of the PA12 used has reacted, alkali metal hydroxide is added in order to neutralize the sulfuric acid (i.e. in particular to set a ph of 7 in the reaction mixture), and then further alkali metal hydroxide is added with which as hydrolysis catalyst the remaining PA12 is reacted.

The alkali metal hydroxide used is especially lithium hydroxide, sodium hydroxide or potassium hydroxide, preferably potassium hydroxide.

This alternative embodiment exploits the fact that the hydrolysis of PA12 having a low content of laurolactam or of the very similar ω-aminolauric acid functions very well with sulfuric acid. When the PA12 has decomposed to a certain extent, the remaining hydrolytic cleavage can then be performed in a subsequent step with alkali metal hydroxides.

This subsequent step can then be preferably be performed as described in DE 3401415 A.

In particular, alkali metal hydroxide is used in such an amount in the subsequent step that, after the neutralization of the sulfuric acid, alkali metal hydroxide remains in such an amount that the ratio of the weights of unconverted polylaurolactam to remaining alkali metal hydroxide is in the range 1:0.1 to 1:1, preferably in the range 1:0.2 to 1:0.8, more preferably in the range 1:0.3 to 1:0.7, even more preferably in the range 1:0.4 to 1:0.6, even more preferably still in the range 1:0.45 to 1:0.51.

The temperature in the subsequent step is preferably in the range 160° C. to 280° C., preferably 180° C. to 250° C., more preferably 200° C. to 230° C.

The pressure in the subsequent is preferably in the range 1 bar to 100 bar, preferably 10 bar to 60 bar.

In the subsequent step the alkali metal hydroxide is preferably used as an aqueous solution, more preferably with a concentration of 1% to 10% by weight of alkali metal hydroxide.

If the subsequent step is performed, the remaining workup of the cleaved PA12 can be performed as described in DE 3401415 A.

The examples which follow illustrate the invention, without limiting said invention in any way.

EXAMPLES

The depolymerization of PA12 having a content of laurolactam and ω-aminolauric acid of in each case<1% was investigated with various catalysts and temperature conditions.

The following catalysts were tested: KOH, $H_2SO_4$, $H_3PO_4$.

The conversion rate was determined using $^1H$ NMR in $CDCl_2$+trifluoroacetic anhydride.

The following tests were carried out:

1. Comparative Test C1. $H_3PO_4$, 320° C.

6.66 mg of PA12 powder were placed in a gold-coated autoclave. Thereafter, 6.8 mg of $H_3PO_4$ (85) and 6.30 mg of water were added and the autoclave was sealed. The autoclave was heated in an oven to 320° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 96%.

2. Comparative Test C2: $H_3PO_4$, 300° C.

5.9 mg of PA12 powder were placed in a gold-coated autoclave. Thereafter, 4.25 mg of $H_3PO_4$ (85) and 5.23 mg of water were added and the autoclave was sealed. The autoclave was heated in an oven to 300° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 35%.

3. Comparative Test C3: $H_3PO_4$, 250° C.

7.17 mg of PA12 powder were placed in a gold-coated autoclave. Thereafter, 4.98 mg of $H_3PO_4$ (85%) and 6.23 mg of water were added and the autoclave was sealed. The autoclave was heated in an oven to 250° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 30° C. and 200 mbar. The conversion rate of the PA12 was 88%.

4. Comparative Test C4: $H_3PO_4$, 220° C.

6.95 mg of PA12 powder were placed in a gold-coated autoclave. Thereafter, 4.6 mg of $H_3PO_4$ (85%) and 6.30 mg of water were added and the autoclave was sealed. The autoclave was heated in an oven to 220° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 87%.

5. Comparative Test C5: $H_3PO_4$, 200° C.

7.27 mg of PA12 powder were placed in a gold-coated autoclave. Thereafter, 5.43 mg of $H_3PO_4$ (85%) and 6.20 mg of water were added and the autoclave was sealed. The autoclave was heated in an oven to 200° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 100%.

6. Inventive Example I1: $H_2SO_4$, 180° C.

6.5 mg of PA12 powder were placed in a gold-coated autoclave. Thereafter, 8.62 mg of $H_2SO_4$ (35%) were added and the autoclave was sealed. The autoclave was heated in an oven to 180° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 100%.

7. Inventive Example I2: $H_2SO_4$, 160° C.

6.61 mg of PA12 powder were placed in a gold-coated autoclave. Thereafter, 8.63 mg of $H_2SO_4$ (35%) were added and the autoclave was sealed. The autoclave was heated in an oven to 160° C. and the reaction mixture was held at this temperature for 4 hours. The mixture was then cooled down to room temperature at a rate of 100 K/min. The reaction mixture was withdrawn from the reactor and neutralized by addition of 1 g of water and a stoichiometric amount of KOH. The mixture was dried at 80° C. and 200 mbar. The conversion rate of the PA12 was 98%.

8. Comparative Test C6 (Corresponding to DE 3407415 A1): KOH, 320° C. 30 g of PA12 powder were placed in a nickel-coated autoclave. Thereafter, 18.95 g of KOH solution (50%) in water were added and the autoclave was sealed. Nitrogen was then injected into the autoclave to 28 bar and it was heated to 320° C. The reaction mixture was held at this temperature for 4 hours. The mixture was then cooled down to room temperature at a rate of 100 K/min and the pressure was released. The reaction mixture was withdrawn from the reactor, dissolved in water and neutralized by addition of 13 g of sulfuric acid. The mixture was dried at and 100 mbar, The conversion rate of the PA12 was 94%.

9. Comparative Test C7 (Corresponding to DE 3407415 A1): KOH, 300° C.

7.42 mg of PA12 powder were placed in a gold-coated autoclave. Thereafter, 4.03 mg of KOH solution (50%) in water were added and the autoclave was sealed. The autoclave was heated in an oven to 300° C. The reaction mixture was held at this temperature for 4 hours and then cooled down to room temperature at a rate of 100 K/min. The mixture was subsequently cooled down to room temperature. The reaction mixture was withdrawn from the reactor and neutralized by addition of 1 g of water and a stoichiometric amount of phosphoric acid. The mixture was dried at and 100 mbar. The conversion rate of the PA12 was 78%.

10. Comparative Test C8 (Corresponding to DE 3407415 A1): KOH, 280° C.

7.17 mg of PA12 powder were placed in a gold-coated autoclave. Thereafter, 4.42 mg of KOH solution (50%) in water were added and the autoclave was sealed. The autoclave was heated in an oven to 280° C. The reaction mixture was held at this temperature for 4 hours and then cooled down to room temperature at a rate of 100 K/min. The mixture was subsequently cooled down to room temperature. The reaction mixture was withdrawn from the reactor and neutralized by addition of 1 g of water and a stoichiometric amount of phosphoric acid. The mixture was dried at and 100 mbar. The conversion rate of the PA12 was 78%.

11. Comparative Test C9 (Corresponding to DE 3407415 A1): KOH, 280° C.

6.80 mg of PA12 powder were placed in a gold-coated autoclave. Thereafter, 0.95 mg of KOH solution (50%) in water were added and the autoclave was sealed. The autoclave was heated in an oven to 320° C. The reaction mixture was held at this temperature for 4 hours and then cooled down to room temperature at a rate of 100 K/min. The mixture was subsequently cooled down to room temperature. The reaction mixture was withdrawn from the reactor and neutralized by addition of 1 g of water and a stoichiometric amount of phosphoric acid. The mixture was dried at and 100 mbar. The conversion rate of the PA12 was 2%.

12. Comparative Test C10: Without Catalyst, 320° C.

7.62 mg of PA12 powder were placed in a nickel-coated autoclave. Thereafter, 3.91 mg of water were added and the autoclave was sealed. The autoclave was heated in an oven to 320° C. The reaction mixture was held at this temperature for 4 hours and then cooled down to room temperature at a rate of 100 K/min. The reaction mixture was withdrawn from the reactor and dried at 80° C. and 200 mbar. The conversion rate of the PA12 was 6%.

Table 1 below summarizes the results of the tests and comparative tests.

TABLE 1

| Test | Amount of PA-12 in mg | Catalyst | Amount of catalyst based on amount of PA-12 in % by weight | Temperature | Yield |
|---|---|---|---|---|---|
| C1 | 6.66 | $H_3PO_4$ | 86.7 | 320° C. | 96% |
| C2 | 5.9 | $H_3PO_4$ | 61.2 | 300° C. | 85% |
| C3 | 7.17 | $H_3PO_4$ | 59.0 | 250° C. | 88% |
| C4 | 6.95 | $H_3PO_4$ | 56.3 | 220° C. | 87% |
| C5 | 7.27 | $H_3PO_4$ | 63.5 | 200° C. | 100% |
| I1 | 6.5 | $H_2SO_4$ | 46.4 | 180° C. | 100% |
| I2 | 6.61 | $H_2SO_4$ | 45.7 | 160° C. | 98% |
| C6 | 30000.0 | KOH | 31.6 | 320° C. | 94% |
| C7 | 7.42 | KOH | 27.1 | 300° C. | 78% |
| C8 | 7.17 | KOH | 30.8 | 280° C. | 78% |
| C9 | 6.8 | KOH | 6.99 | 320° C. | 2% |
| C10 | 7.62 | — | — | 320° C. | 6% |

It is evident from the results that the addition of $H_2SO_4$ results in almost quantitative conversion at particularly low temperatures, i.e. as low as at 190° C. and 160° C.

13. Temperature Dependence of the Hydrolysis of PA12 with Sulfuric Acid

In order to investigate the temperature dependence of the hydrolysis of PA12 with sulfuric acid, the following series of tests was carried out:

PA12 powder and $H_2SO_4$ (35%) were added to a gold-coated autoclave in the amounts respectively indicated in Table 2 below. The autoclave was then sealed. The autoclave was heated in an oven to the respective temperature T indicated in Table 2 below (heating rate 5 K/min) and the reaction mixture was held at this temperature for 4 hours. The mixture was then cooled down to room temperature at a rate of 5 K/min. The residual content of PA12 was subsequently determined.

TABLE 2

| Test | Amount of PA-12 in mg | Added amount of 35% $H_2SO_4$ in mg | Temperature T | Residual content of PA12 |
|---|---|---|---|---|
| C11 | 5.33 | 5.08 | 80° C. | 90.5% |
| I3 | 5.47 | 5.33 | 125° C. | 7.3% |
| I4 | 5.7 | 4.99 | 158° C. | 6.3% |
| I5 | 6.22 | 5.32 | 190° C. | 5.3% |
| C12 | 6.3 | 5.1 | 230° C. | 10.5% |
| C13 | 6.74 | 12.68 | 80° C. | 7.2% |
| I6 | 5.60 | 12.07 | 125° C. | <0.1% |
| I7 | 5.03 | 13.04 | 158° C. | 1.3% |
| I8 | 6.78 | 12.07 | 190° C. | 0.7% |
| C14 | 5.74 | 13.23 | 230° C. | 3.2% |

It is apparent from the test results shown in Table 2 that the hydrolysis of PA12 with sulfuric acid in the temperature range from 125° C. to 190° C. (13 to 15; 16 to 18) proceeds surprisingly efficiently. In comparison, hydrolysis at a temperature of 80° C. (comparative tests C11, C13) performed in the prior art (U.S. Pat. No. 4,170,588 A) is not productive. Comparative tests C12 and C14 additionally demonstrate that at a temperature of 230° C. the residual content of PA12 rises again; hence the efficiency of the conversion decreases again.

The invention claimed is:

1. A process for hydrolysis of polylaurolactam, the process comprising:
    cleaving the polylaurolactam with sulfuric acid at a temperature of from 125° C. to 190° C., to give o-aminolauric acid.

2. The process according to claim 1, wherein the polylaurolactam has a molar mass of 1,000 to $10^6$ g/mol.

3. The process according to claim 1, wherein the polylaurolactam has a content of laurolactam of <4.9% by weight.

4. The process according to claim 1, wherein the polylaurolactam has a content of ω-aminolauric acid of <4.9% by weight.

5. The process according to claim 1, wherein a pressure is 1 bar to 100 bar.

6. The process according to any claim 1, wherein a ratio of a weight of the sulfuric acid to a weight of the polylaurolactam is in a range of 1:0.1 to 1:1.

7. The process according to claim 1, further comprising:
    after 1-99% by weight of the polylaurolactam has reacted, adding alkali metal hydroxide to neutralize the sulfuric acid, and then adding further alkali metal hydroxide with which a remaining amount of the polylaurolactam is reacted.

8. The process according to claim 7, wherein after the neutralization of the sulfuric acid, the alkali metal hydroxide remains in such an amount that a ratio of a weight of unconverted polylaurolactam to a weight of a remaining amount of the alkali metal hydroxide is in a range of 1:0.1 to 1:1.

9. The process according to claim 7, wherein a temperature while adding the alkali metal hydroxide is in a range of 160° C. to 280° C.

10. The process according to claim 7, wherein a pressure while adding the alkali metal hydroxide is in a range of 1 bar to 100 bar.

* * * * *

UNITED STATES PATENT AND TRADEMARK OFFICE
CERTIFICATE OF CORRECTION

| | | |
|---|---|---|
| PATENT NO. | : 12,351,538 B2 | Page 1 of 1 |
| APPLICATION NO. | : 18/245317 | |
| DATED | : July 8, 2025 | |
| INVENTOR(S) | : Alexander Richter et al. | |

It is certified that error appears in the above-identified patent and that said Letters Patent is hereby corrected as shown below:

In the Claims

Column 8, Lines 29-30, Claim 1, currently reads, "give o-aminolauric acid" and should read --give ω-aminolauric acid.--.

Signed and Sealed this
Eighteenth Day of November, 2025

John A. Squires
*Director of the United States Patent and Trademark Office*